United States Patent
Li (10) Patent No.: US 9,958,425 B1
(45) Date of Patent: *May 1, 2018

(54) QUANTUM DOT-POLYMER NANOCOMPOSITE SENSOR ARRAY FOR CHEMICAL VAPOR SENSING

(71) Applicant: THE MITRE CORPORATION, McLean, VA (US)

(72) Inventor: Sichu Li, Fairfax, VA (US)

(73) Assignee: The Mitre Corporation, McLean, VA (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/426,412

(22) Filed: Feb. 7, 2017

Related U.S. Application Data (62) Division of application No. 14/804,667, filed on Jul. 21, 2015, now Pat. No. 9,599,564.

(51) Int. Cl.
G01N 33/00 (2006.01)
G01N 21/64 (2006.01)

(52) U.S. Cl.
CPC ....... *G01N 33/0031* (2013.01); *G01N 21/643* (2013.01); *G01N 2021/6441* (2013.01)

(58) Field of Classification Search
CPC ............. G01N 33/0031; G01N 21/643; G01N 2021/6441
USPC ........... 524/556; 438/89, 962; 257/441, 465, 257/466
See application file for complete search history.

(56) References Cited

PUBLICATIONS

C. Bright et al. "Quantum Dot and Polymer Composite Cross-Reactive Array for Chemical Vapor Detection", Anal. Chem., 2015, 87, pp. 12270-12275.*
H. Xu et al. "Detecting hydrogen sulfide by using transparent polymer with embedded CDSe/CdS quantum dots", Sensors and Actuators, B: Chemical (2010), 143(2), pp. 535-538.*
Nath et al. "PVA embedded ZnO quantum dots for methanol sensing", NanoTrends (2010), 8(3), pp. 1-6.*
R. Potyrailo et al. "Multisize CdSe Nanocrystal/Polymer Nanocomposites for Selective Vapor Detection Identified from High-Throughput Screening Experimentation", ACS Combinatorial Science (2012), 14(3), 170-178.*
I. Gorelikov & E. Kumacheva. Electrodeposition of polymersemiconductor nanocomposite films. Chem Mater 2004; 16:4122-27.
D. Kaushik, et al. Synthesis and characterisation of electropolymerised polyaniline/Q-ZnSe composite films. Mater Lett 2006; 60:2994-97.
M. Y. Gao, et al. Synthesis of PbS nanoparticles in polymer matrices. Chem Commun 1994: 2779-80.
Y. Yang, et al. Preparation, characterization and electroluminescence of ZnS nanocrystals in a polymer matrix. J Mater Chem 1997; 7:131-33.
Y. Yang, et al. Electroluminescence from ZnS/CdS nanocrystals/polymer composite. Synth Met 1997; 91:347-49.
C. L. Lü, et al. PbS/polymer nanocomposite optical materials with high refractive index. Chem Mater 2005; 17:2448-54.
J. Y. Wang, et al. Controlled fabrication of cross-linked nanoparticles/polymer composite thin films through the combined use of surface-initiated atom transfer radical polymerization and gas/solid reaction. J Am Chem Soc 2002; 124:13358-59.
T. Cui, et al. CdS-nanoparticle/polymer composite shells grown on silica nanospheres by atom transfer radical polymerization. Adv Fund Mater 2005; 15:481-86.
O. V. Salata, et al. Fabrication of PbS nanoparticles embedded in a polymer film by a gas-aerosol reactive electrostatic deposition technique. Adv Mater 1994; 6:772-75.
O. V. Salata, et al. Uniform GaAs quantum dots in a polymer matrix. Appl Phys Lett 1994; 65:189-91.
O. V. Salata, et al Fabrication of CdS nanoparticles embedded in a polymer film by gas aerosol reactive electrostatic deposition technique. Thin Solid Films 1994; 251:1-3.
Y. Wang, et al. PbS in polymers. From molecules to bulk solids. J Chem Phys 1987; 87:7315-22.
J. Lee, et al. Full color emission from II-VI semiconductor quantum dot—polymer composites. Adv Mater 2000; 12:1102-05.
L. Pang, et al. PMMA quantum dots composites fabricated via use of pre-polymerization. Opt Express 2005; 13:44-49.
L. Martiradonna, et al. Nanopatterning of colloidal nanocrystals emitters dispersed in a PMMA matrix by e-beam lithography. Microelectr Eng 2006; 83:1478-81.
B. Ballou, et al. Noninvasive imaging of quantum dots in mice. Bioconjugate Chem 2004; 15:79-86.
X. Gao, et al. In-vivo cancer targeting and imaging with semiconductor quantum dots, Nature Biotechnology 2004; 22:969-76.
M. Y. Han, et al. Quantum-dot-tagged microbeads for multiplexed optical coding of biomolecules, Nature Biotechnology 2001; 19:631-35.
G. N. Guo, et al. Preparation and characterization of novel CdSe quantum dots modified with poly (d,l-lactide) nanoparticles. Mater Lett 2006; 60:2565-68.
X. Michalet, et al. Quantum dots for live cells, in vivo imaging, and diagnostics. Science 2005; 307:538-44.
P. Sharma, et al. Nanoparticles for bioimaging. Adv Colloid Interface Sci 2006; 123:471-85.
S. P. Mulvaney, et al. Incorporating fluorescent dyes and quantum dots into magnetic microbeads for immunoassays. BioTechniques 2004; 36:602-09.

(Continued)

*Primary Examiner* — Michael M Bernshteyn
(74) *Attorney, Agent, or Firm* — Rosenberg, Klein & Lee (57) ABSTRACT

A method of detecting the presence of a chemical vapor of interest using a quantum dot-polymer nanocomposite sensor array is provided. The method includes forming a plurality of sensors respectively of different nanocomposite films and a plurality of QDs. The plurality of sensors are exposed to a target chemical vapor and impingement by an excitation light source. Fluorescence emission intensity of the sensors is measured for a preselected duration of time and then the sensors are placed into contact with a chemical vapor. The changes in fluorescence emission intensity for all sensors are detected over time and the combined changes in fluorescence are compared to establish a unique combined response to identify the target chemical vapor.

8 Claims, 8 Drawing Sheets

(56) References Cited

PUBLICATIONS

S. J. Rosenthal. Bar-coding biomolecules with fluorescent nanocrystals. Nat Biotechnol 2001; 19:621-22.

N. Gaponik, et al. Toward encoding combinatorial libraries: charge-driven microencapsulation of semiconductor nanocrystals luminescing in the visible and near IR. Adv Mater 2002; 14:879-82.

C. Kirchner, et al. Cytotoxicity of nanoparticle-loaded polymer capsules. Talanta 2005; 67:486-91.

B. Zebli, et al. Magnetic targeting and cellular uptake of polymer microcapsules simultaneously functionalized with magnetic and luminescent nanocrystals. Langmuir 2005; 21:4262-65.

R. Bashir, et al. Micromechanical cantilever as an ultrasensitive pH microsensor. Appl Phys Lett 2002; 81:3091-93.

C. Ruan, et al. A mass-sensitive pH sensor based on a stimuli responsive polymer. Anal Chem Acta 2003; 497:123-31.

M. Kuang, et al. Fabrication of multicolor-encoded microspheres by tagging semiconductor nanocrystals to hydrogel spheres. Adv Mater 2005; 17:267-70.

R. A. Potyrailo, et al. Multisize CdSe nanocrystal/polymer nanocomposites for selective vapor detection identified from high-throughput screening experimentation. ACS Comb Sci 2012; 14:170-78.

C. J. Bright, et al. Quantum dot and polymer composite cross-reactive array for chemical vapor detection. Anal Chem 2015; 87:12270-75.

S. P. Mondal, et al. CdSe quantum dots-poly(3-hexylthiophene) nanocomposite sensors for selective chloroform vapor detection at room temperature. Appl Phys Lett 2012; 101:173108/1-4.

\* cited by examiner

QUANTUM DOT-POLYMER NANOCOMPOSITE SENSOR ARRAY FOR CHEMICAL VAPOR SENSING

CROSS-REFERENCE TO RELATED APPLICATIONS

This application is a Divisional patent application of co-pending application Ser. No. 14/804,667, filed on 21 Jul. 2015, now pending. The entire disclosure of the prior application Ser. No. 14/804,667, is considered a part of the disclosure of the accompanying Divisional application and is hereby incorporated by reference.

FIELD OF THE INVENTION

The subject invention relates generally to the field of chemical vapor sensing. In particular, the invention relates to a sensor array for sensing chemical vapors. More specifically, the invention relates to incorporating fluorescent quantum dots into a polymer network to form a sensor and utilizing a plurality of sensors to form an array. Each of the sensors includes a polymer that is responsive to a particular chemical analyte or group of chemical analytes, and quantum dots which fluorescence alters when the polymer responds to an analyte, whereby changes in fluorescence can be measured from all sensors in the array and exploited for detecting the presence or a change in concentration of particular chemical vapor. A unique combined response pattern from all of the sensors in the array allows the array to distinguish one vapor from others, and thus provides detection specificity. Several alternative arrays and methods for their synthesis, as well as the method of utilizing the arrays to detect the presence of a particular chemical vapor are presented.

BACKGROUND OF THE INVENTION

The present disclosure relates generally to quantum dot-polymer nanocomposites for chemical vapor sensing. In particular, the subject application relates to quantum dot-polymer nanocomposite sensor arrays for detecting vapors of a defined group of chemical analytes. More in particular, the subject application relates to the incorporation of quantum dots into a polymer matrix to form a film wherein the polymer is known to be responsive to a selective group of chemical vapors. Thereby, when the film is placed into contact with a chemical vapor, interaction between functional groups on the polymer and the chemical generate changes in the polymer network. Expansion or contraction of the polymer network responsive to interaction of the polymer and chemical generate measurable changes in fluorescence by virtue of the incorporated quantum dots.

Quantum Dots (QDs) are semiconductor nanocrystals which are known for their unique size-tunable optical and electronic properties. For the past few decades, extensive amounts of time, energy, and funding have been devoted to research and development efforts exploring the use of quantum dots (QDs) in a variety of different areas, for example, biological labeling for imaging and monitoring and optical sensing for chemical and biological detection. In the context of chemical and biological sensing applications, QDs must be functionalized on their surfaces, or embedded in a solid state matrix to form a composite. This is necessary to avoid QD agglomeration and the consequent fluorescence quenching.

Attributed to their transparence in the ultraviolet-visible (UV-Vis) region of the electromagnetic spectrum, polymeric materials are suitable candidates to be utilized as matrices for quantum dot composites in optical sensing applications.

Current fluorescence sensor technologies for chemical and biological detection are based on detecting changes in fluorescence caused by either a reaction between an organic fluorophore and a target or fluorescence resonance energy transfer (FRET) between two chromophores. The major problem associated with sensing mechanisms which use organic fluorophores is the resultant photo-bleaching and with FRET, it is difficult to control operation conditions. Neither mechanism is suitable for use under ambient air conditions.

Therefore, there is a need for a chemical detection sensing system which is suitable for use in ambient air conditions and which is more sensitive and robust than conventional sensing mechanisms.

By incorporating quantum dots into a polymer network structure to form a nanocomposite sensor or a nanocomposite sensor array, the quantum dots act as optical indicators for optical sensing applications, namely for chemical vapor detection, classification and identification.

SUMMARY OF THE INVENTION

A quantum dot-polymer nanocomposite sensor array for chemical vapor sensing is provided. The quantum dot-polymer nanocomposite sensor array comprises an array of sensors for detecting vapors of any of a defined group of chemical analytes. The array of sensors includes a plurality of sensors respectively formed by different nanocomposite films. Each of the nanocomposite films includes a different polymer that is correspondingly responsive to at least one of the chemical analytes and fluorescent QDs. The plurality of sensors are disposed on a substrate for impingement by an excitation light source. Responsive to exposure to a vapor of any one of the chemical analytes, the combined fluorescence response of the plurality of sensors uniquely identifies the chemical analyte.

In another aspect, a method of forming a quantum dot-polymer nanocomposite sensing film for chemical vapor sensing is provided. First, a mass of a type of polymer known to be responsive to a selective group of chemical vapors is obtained and a quantum dot (QD) suspension is obtained. Then, the polymer is mixed with a solvent until a clear polymer solution results and the QD suspension is dried until the suspension becomes wax-like. Next, the dried QDs are added to the polymer solution and thereafter, the dried QD and polymer solution are mixed to form the precursor solution. At least a portion of the precursor solution is then deposited onto a substrate and the mixture is spread thereon. Finally, the precursor solution is air-dried to form the quantum dot-polymer nanocomposite sensing fil.

From another aspect, a method of detecting the presence of a chemical vapor of interest begins with manufacturing a plurality of quantum dot polymer nanocomposite sensing films wherein each of the sensing films comprises a plurality of quantum dots (QDs) doped into a polymer network to form a film wherein the polymer network is known to be responsive to a selective group of chemical vapors. The quantum dot polymer nanocomposite films are impinged by an excitation light source and then the sensing films are exposed to a suspected contaminant. Next, the change in fluorescence emission intensity from the films is detected that is responsive to the excitation light source over time and the suspected contaminant. Thereafter, the changes in fluorescence emission intensity from the films are compared to establish a unique combined response.

DETAILED DESCRIPTION OF THE PREFERRED EMBODIMENTS

In general, the terms and phrases used herein have their art-recognized meaning, which can be found by reference to standard texts, journal references, and context known to those skilled in the art. The phrase "target chemical analytes" denotes chemical analytes to which at least a subset of sensors in a given quantum dot-polymer nanocomposite sensor array will respond.

The following details are intended to explain the inventive concept of the subject Patent Application. However, such are provided for illustrative purposes and not intended to limit the scope of the invention. It will be apparent to those skilled in the art that a number of substitutions of, for example, different quantum dots, polymers and chemical compounds may be made without departing from the scope of the invention.

In general concept, the subject Application is directed to a quantum dot-polymer nanocomposite sensor array for chemical vapor sensing, a method of forming the quantum dot-polymer nanocomposite sensor array and a method of detecting the presence of a chemical vapor of interest.

The quantum dot-polymer nanocomposite sensor array comprises an array of sensors suitable for detecting vapors of a defined group of chemical analytes. The plurality of sensors that form the array are made of a nanocomposite film wherein each film includes a polymer which is responsive to at least one chemical analyte of interest.

Figure 1:
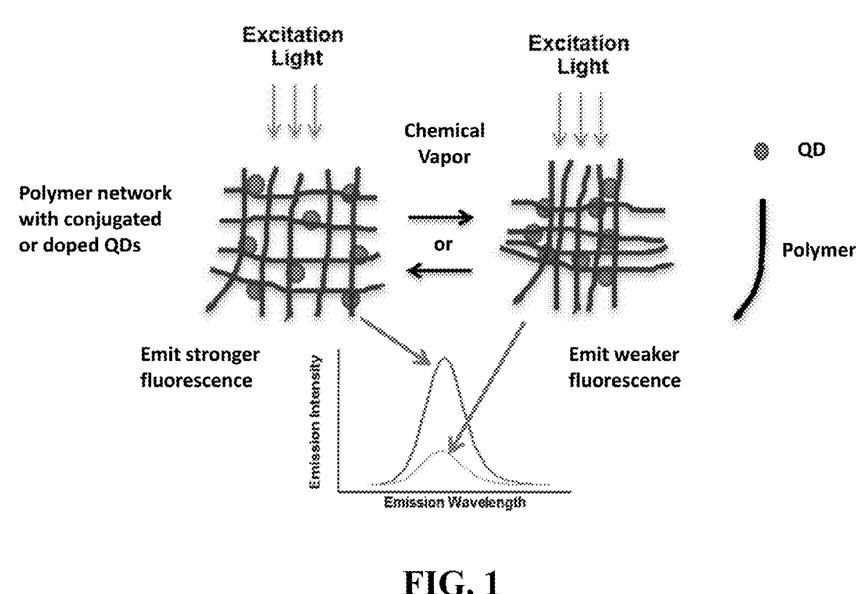
FIG. 1 is a schematic illustration of the change in spacing of a QD-polymer network responsive to the presence of a particular chemical analyte.

The sensors are disposed on a substrate for impingement by an excitation light source. When the sensors are exposed to one of the chemical analytes of the group, one of three things happens to the polymer network: it expands, it contracts or it remains the same. FIG. 1 provides a schematic illustration of the change in spacing, in other words, the expansion or contraction of a QD-polymer network responsive to the presence of a particular chemical vapor. Expansion of the QD-polymer network is associated with a corresponding increase in fluorescence intensity while contraction of the network brings about a decrease in fluorescence intensity. Maintenance of the same level of fluorescence indicates that the polymer network did not expand or contract in response to the chemical vapor with which it was placed in contact.

Figure 2:
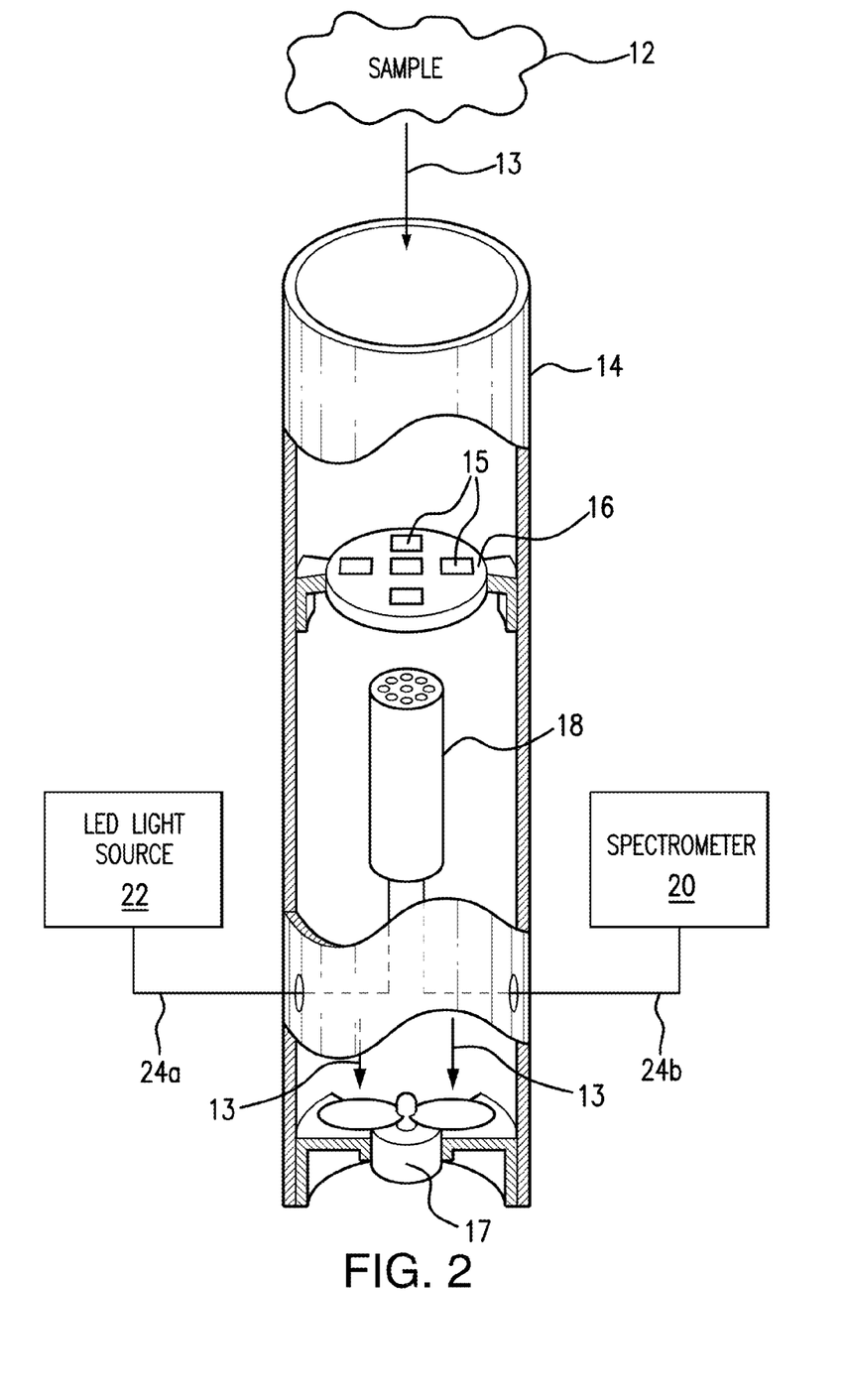
FIG. 2 is a schematic illustration of an operational test device for testing the responsiveness of sensors to chemical analytes.

An exemplary operational test device (also referred to herein as a test system) used for testing the responsiveness of sensors to chemical analytes is provided in FIG. 2. Such a test system includes generally an air sampler tube 14, a probe 18, an LED light source 22 and a spectrometer 20. The LED light source 22 and spectrometer 20 are connected to the probe 18, respectively, by optical fibers 24a and 24b. A sensing film (which includes substrate 16 and sensors 15) is disposed between the air sampler tube 14 inlet and the probe 18, and a fan 17 is disposed beneath the probe 18 to circulate air through the system. For instance, a sample 12 containing a target chemical analyte is disposed above the air sampler tube 14 inlet and the fan 17 causes air to flow through the device in a predetermined direction shown by directional arrows 13. The fan 17 brings the target chemical analyte of the sample 12 to come into contact with the sensing film to enable the system to determine whether a target chemical analyte is present in the sample 12. Alternative devices for effectuating air flow through the system may be employed such as, for example, a blower disposed external to the air sampler tube 14 to blow the sample 12 into air sampler tube 14.

After the sample 12 is brought into contact with the sensing film, excitation light is transmitted from the LED light source 22 to the probe 18 through optical fiber 24a. The substrate 16 is transparent or at least light transmissive. For example, the substrate 16 may be a transparent plastic film, a glass slide, or a top surface of the glass fiber of the probe 18, whereby sensors 15 on the upper surface of the sensor substrate 16 are excited by light from LED light source 22 of probe 18 through the substrate 16. When the glass fiber is the substrate, a different sensor is deposited on each fiber and the illumination source is provided external to the probe. In response, emission light collected from the sensor substrate 16 is transmitted to the spectrometer 20 through optical fiber 24b. A computer (not shown in FIG. 2) interfaces with the spectrometer 20 to retrieve the signal and process the data.

The components of the test device are commercially available products and are shown herein for exemplary purposes only. Suitable alternatives may be made for the individual components shown in FIG. 2.

Figure 7:
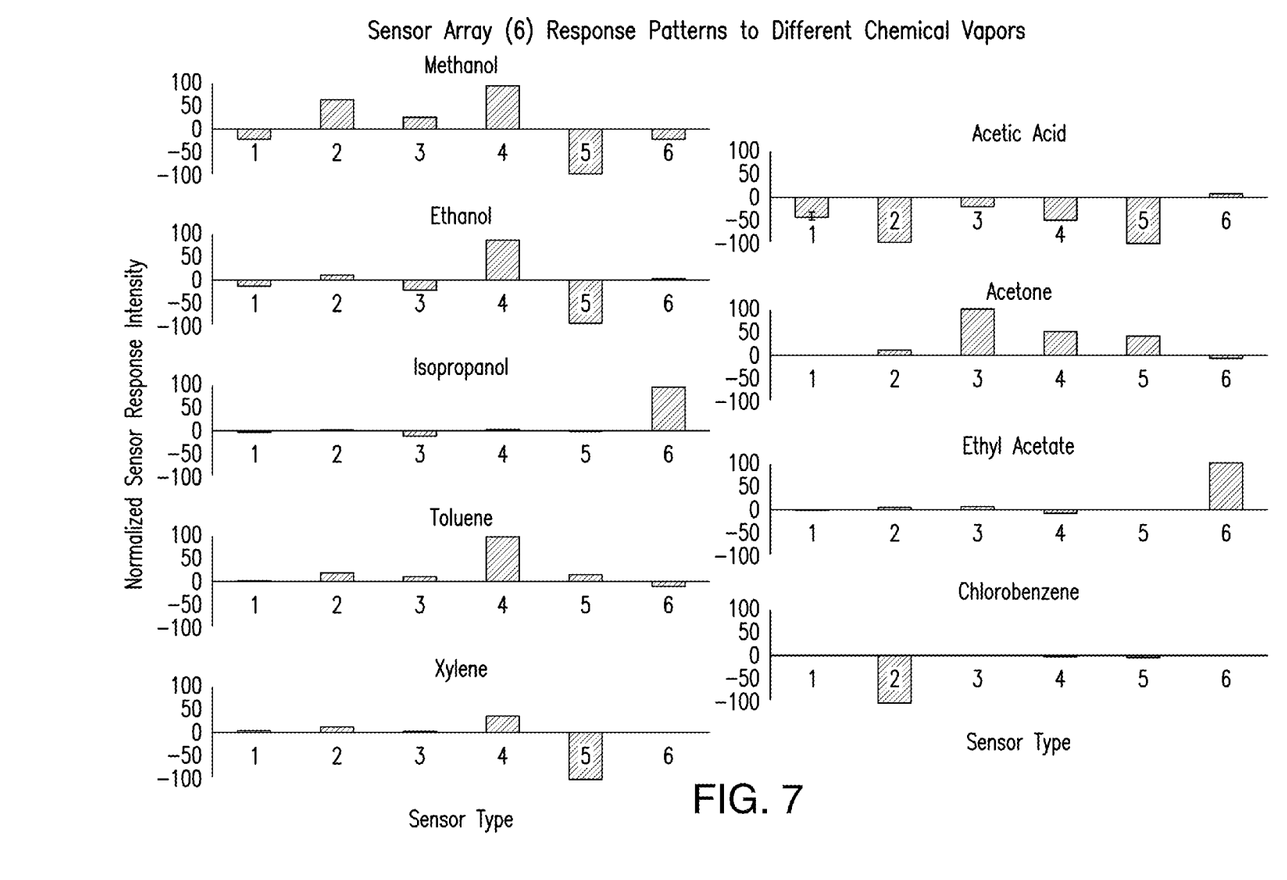
FIG. 7 is a bar graph showing normalized responses of a six sensor array to 9 different chemical vapors.
Figure 8:
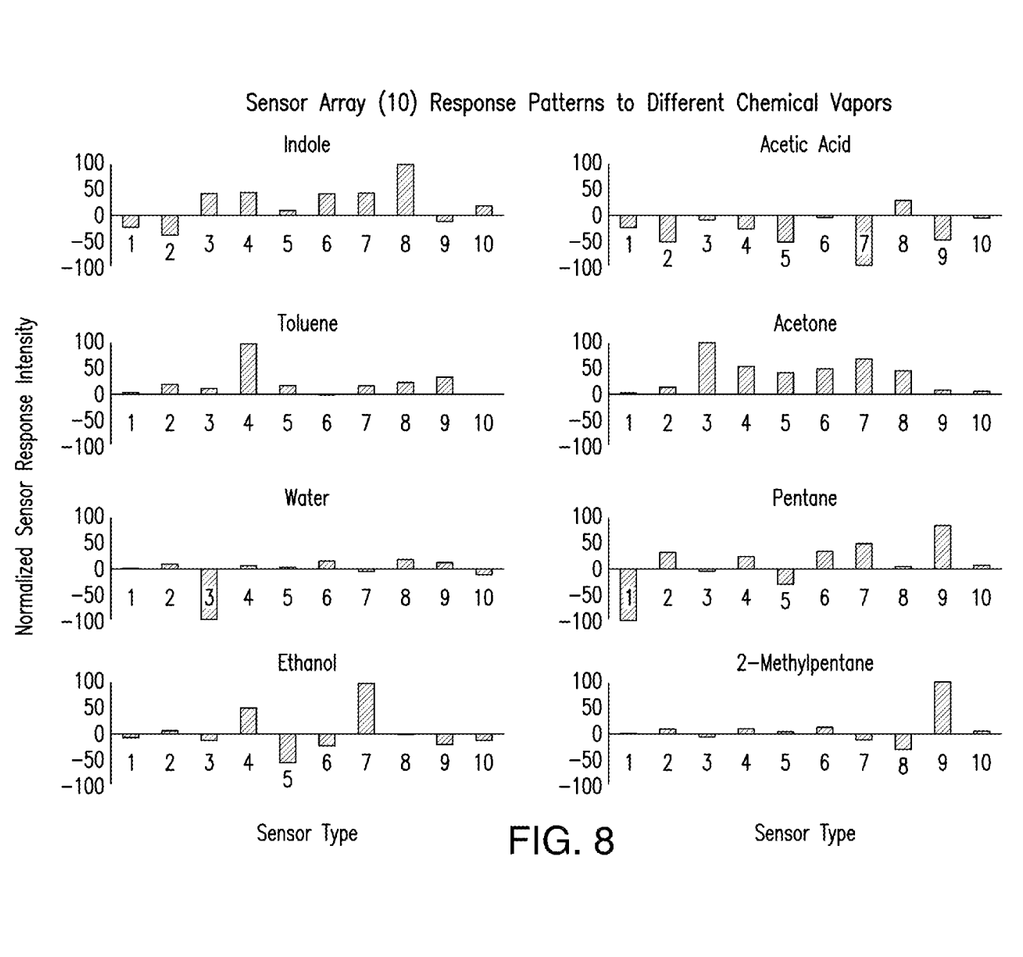
FIG. 8 is a bar graph showing normalized responses of a ten sensor array to 8 different chemical vapors.

Utilizing such systems, a sensor response is obtained for each sensor of the array. The response is based upon fluorescence changes before and after exposure to a particular chemical. The signal detector reads the fluorescence signals that are subsequently processed to obtain the rates of change for comparison. The responses are categorized as "positive," "negative" or "zero." A polymer network expansion in the presence of a particular chemical vapor causes a corresponding increase in fluorescence which is a "positive" response while a polymer network contraction in the presence of a chemical vapor causes a corresponding decrease in fluorescence which is a "negative" response. A "zero" response is one which is at noise level and can therefore be neglected. FIGS. 7 and 8 respectively show the responsiveness of a six sensor array and a ten sensor array to a variety of different chemical analytes.

Though certain polymers are discussed herein with respect to the exemplary embodiments, there are a multitude of additional polymers that are useful for forming a sensor array. Suitable polymer candidates do not absorb the excitation light of the associated quantum dots and they are soluble or able to swell in a certain solvent. The polymer solution must also be capable of being deposited on a substrate to form a film and must exhibit reactivity to certain target analytes.

Design of the sensors of the QD-polymer nanocomposite sensor array is based upon the reactivity of the functional groups associated with and the polarity of the polymer along with the size of the target analyte. The reactivity of the functional group on the polymer used determines to which functional group it will respond on the target chemical of interest.

Polarity of the polymers can be used to discriminate between hydrophilic and hydrophobic analytes. Polarity is also useful for differentiating chemical analytes of interest when those chemical targets have the same functional group, for instance, targets which simply differ in the number of carbon backbones that they possess. Molecular weight of the polymers can also be utilized as a parameter for designing the individual sensors making up the array. For instance, a polymer having a relatively lower molecular weight will be able to react much more quickly with smaller molecular analytes.

TABLE 1.1 lists a number of common polymers along with a representative sampling of target chemical vapors with which the polymers will react to elicit a measurable change.

TABLE 1.1

| Polymer | Target Chemical Vapors |
|---------|------------------------|
| Polystyrene | aromatic hydrocarbons (e.g., benzene, toluene, xylene, ethylbenzene); chlorinated aliphatic hydrocarbons (e.g., methylene chloride, chloroform, carbon tetrachloride); ketones (e.g., acetone, methyl ethyl ketone, diisopropyl ketone); cyclohexane, alkyl-cyclohexanes (e.g., methylcyclohexane, ethylcyclohexane); esters (e.g., ethyl acetate, butyl acetate); pyridine; dioxane; dimethylformamide; cyclohexanone; tetrahydrofuran; n-butyl phthalate; methyl phthalate;, ethyl phthalate; tetrahydrofurfuryl alcohol; 1-nitro-propane; carbon disulfide and tributyl phosphate |
| Poly (para- -substituted styrene), including poly-4-methoxystyrene, poly-4-methyl-styrene, poly-α-methylstyrene, poly-4-tert-butyl-styrene, poly-4-chlorostyrene, poly-4-bromostyrene | aromatic hydrocarbons (e.g., benzene, toluene, xylene); chloroform; carbon tetrachloride; dichloromethane (DCM); dichloroethane (DCE; and tetrahydrofuran (THF) |
| Polystyrene-co-allyl alcohol | ketones (e.g. methyl ethyl ketone); toluene; acids (acetic acid) and tetrahydrofuran |
| Polystyrene-co-butadiene | aromatic hydrocarbons (e.g., benzene, toluene, xylene); tetrahydrofuran; alkane (e.g., hexane) |
| Poly-2-hydroxyethyl methacrylate | water; alcohols and acids (e.g., acetic acid) |
| Polymethyl-methacrylate | alcohols (e.g., methanol, ethanol); ketones (e.g., acetone);, esters (e.g., methyl acetate, ethyl acetate); chlorinated solvents (e.g., dichloromethane, trichloromethane, chloroform) and acids (e.g., acetic acid) |

TABLE 1.1-continued

| Polymer | Target Chemical Vapors |
|---------|------------------------|
| poly-4-vinylphenol | alcohols (e.g., methanol, ethanol, 2-propyl alcohol, t-butyl alcohol); ketones (e.g., acetone); acetonitrile; dioxane; THF and DMSO |
| Poly-4-vinylphenol-co-methyl methacrylate | alcohols (e.g., methanol, ethanol,, 2-propyl alcohol, t-butyl alcohol); ketones (e.g., acetone); esters (e.g., methyl acetate, ethyl acetate);, chlorinated solvents (e.g., dichloromethane, trichloromethane, chloroform) and acids (e.g., acetic acid) |
| polyethyleneimine | Water |
| Hydroxypropyl cellulose | water; alcohols and anhydrous solvents (e.g., polar organic solvents and glycols) |
| Polybisphenol-A-carbonate | chlorinated solvents (e.g., carbon tetrachloride or methylene chloride) |
| Polysulfone | chlorinated hydrocarbons (e.g., carbon tetrachloride or dichloromethane) |
| Polyvinylidene fluoride | dimethyl sulfoxide or tetrahydrofuran |
| Polycaprolactone | Tetrahydrofuran and chloroform, esters (e.g. ethylacetate) |
| polyethylene glycol | Water; alcohols, ketones (e.g, acetone) and acids (e.g., acetic acid) |
| Poly-N-vinyl pyrrolidone | Water; polar solvents including alcohols, ketones (e.g., acetone) and acids (e.g., acetic acid) |
| polyethylene-co-vinyl acetate | Tetrahydrofuran; aromatic hydrocarbons (e.g., benzene, toluene and xylene);, cyclohexane and chlorinated solvents (e.g., chloroform and o-dichlorobenzene) |

Figure 3:
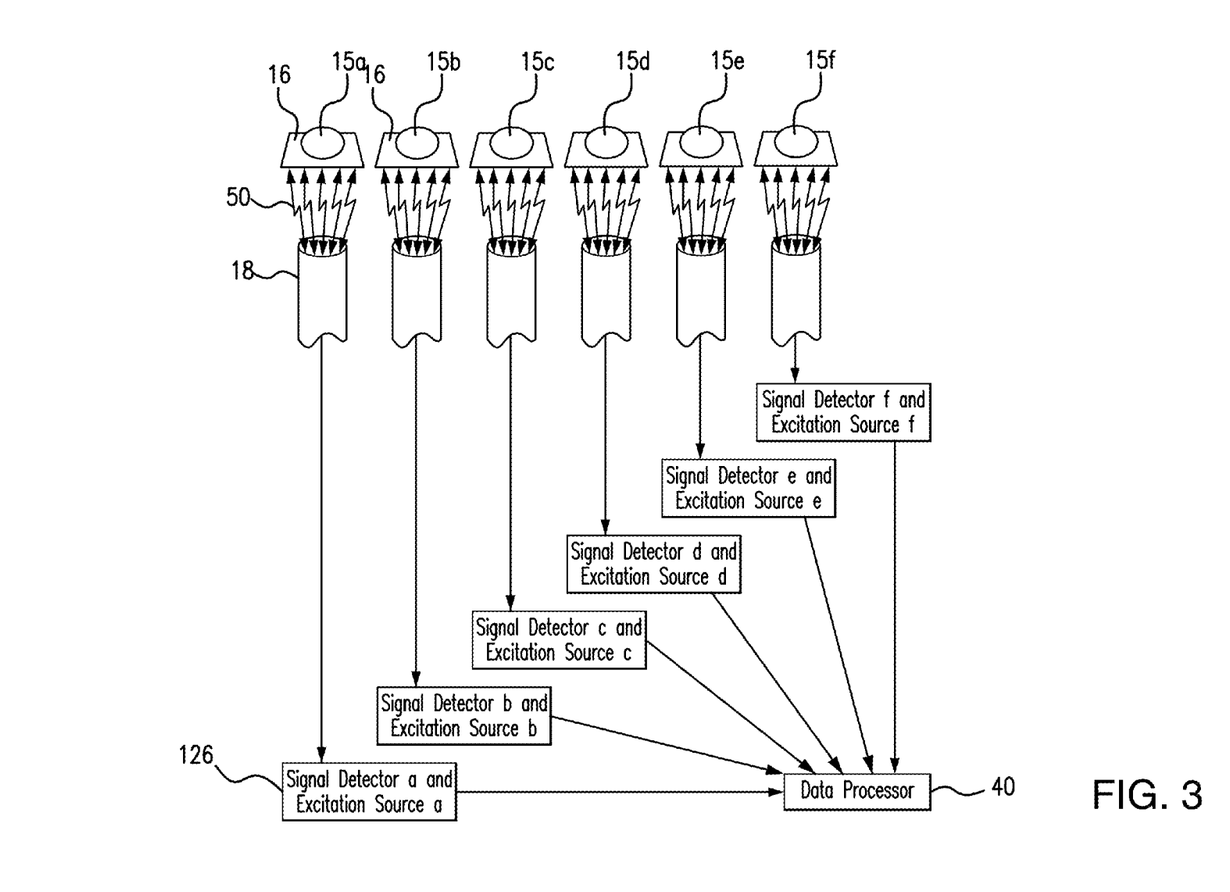
FIG. 3 is a schematic illustration of an optical detection system for detecting the presence of a chemical vapor of interest using separate excitation light sources.

In certain exemplary embodiments, the sensor array is designed such that the quantum dots of each sensing film have the same emission wavelength. In such instances, each sensor/sensing film is individually excitable thereby enabling separate and independent detection of the changes in fluorescence emission intensity of each sensor. FIG. 3 provides an example of the set up for exciting each of the sensing films by an independent excitation light source. As shown in FIG. 3, each sensor substrate 16 has a sensor 15a-15f disposed thereon to form a sensing film. Each sensing film is associated with an independent probe 18 and an independent detection system 126 which includes a signal detector (a-f) and an excitation source (a-f). Each excitation source (a-f) is an LED light source and each signal detector (a-f) is a spectrometer which are connected to the respective probe via optical fibers.

Figure 4:
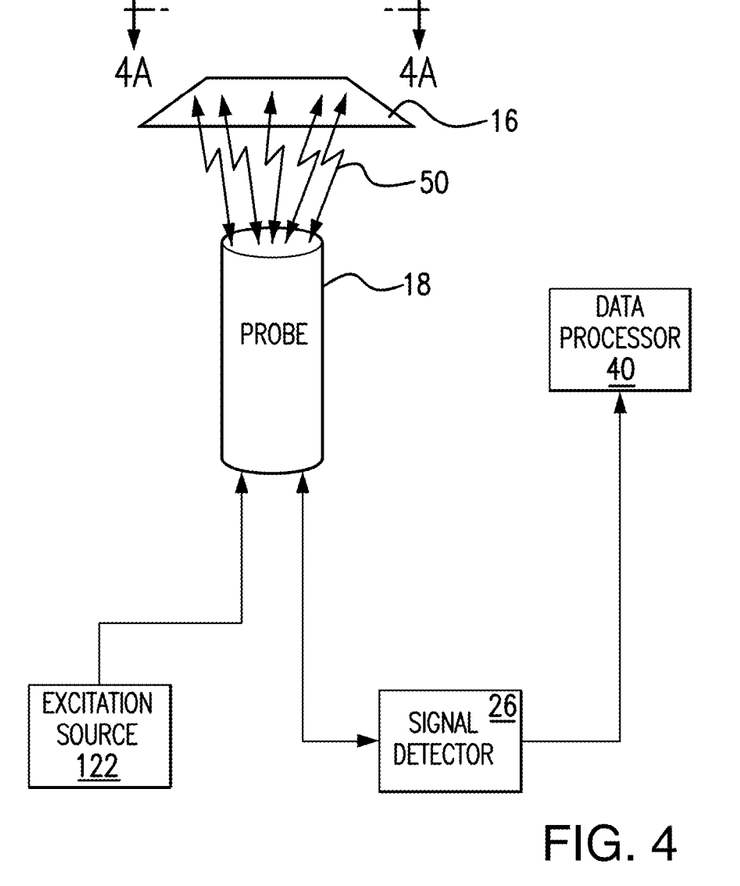
FIG. 4 is a schematic illustration of an optical detection system for detecting the presence of a chemical vapor of interest using a common excitation light source.
Figure 5:
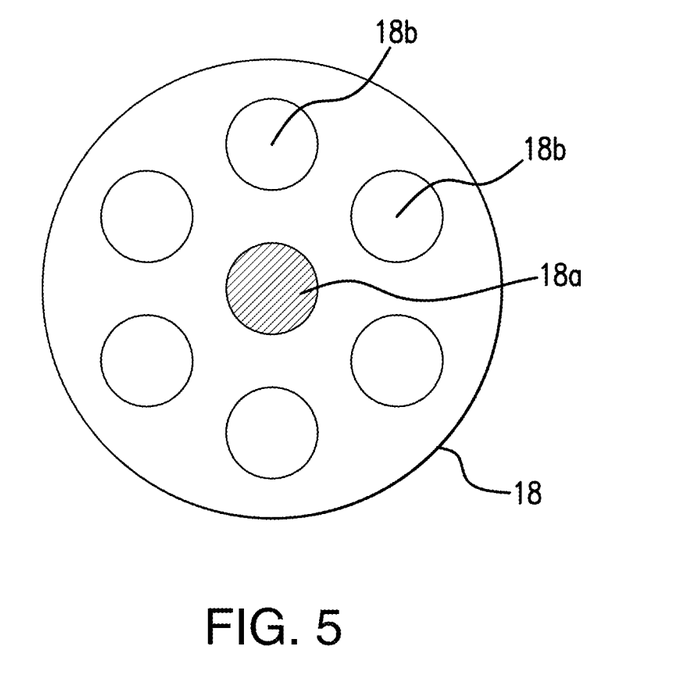
FIG. 5 is a cross sectional view of a probe used in conjunction with the optical detection systems shown in FIGS. 3 and 4.

Each probe 18 includes an optical fiber for providing excitation light (not shown for simplicity) which is different for each of the six sensors. Each probe 18 also has a plurality of optical fibers for providing emission light wherein the emission light associated with each of the plurality of optical fibers is the same. FIG. 5 is a cross-sectional view of a commercially-available probe used in conjunction with the systems depicted in FIGS. 3 and 4. These probes 18 are optical components which include a fiber 18a to bring excitation light to the sensing film and another fiber (or fibers) 18b to collect emission light from the sensing film. The use of multiple fibers to collect light is for the purpose of signal amplification.

As shown in FIG. 3, emission and excitation light rays 50 are exchanged between the probes 18 and sensing films. An excitation source (a-f) of detection system 126 transmits excitation light, via the optical fiber for excitation light 18a (shown in FIG. 5), such that excitation light passes through substrate 16 to excite the respective sensor 15 (a-f). The emission light is collected by and transmitted through optical fibers for emission light 18b (shown in FIG. 5) and a signal detector (a-f) of detection system 126 measures the fluorescence signal which is subsequently processed by the data processor 40 to determine the rate of change. The sensor response to a target analyte results in a change in polymer network structure. The later causes a light scattering effect that alters the detected QD fluorescence. The change in fluorescence intensity and/or rate of change is measured to detect the presence of a target analyte.

Six sensor films including sensors 15a-15f and their corresponding sensor substrates 16 are depicted in FIG. 3, however such is provided for exemplary purposes only and it should be appreciated that the number of sensors may vary depending upon the particular application and objectives.

Figure 4A:
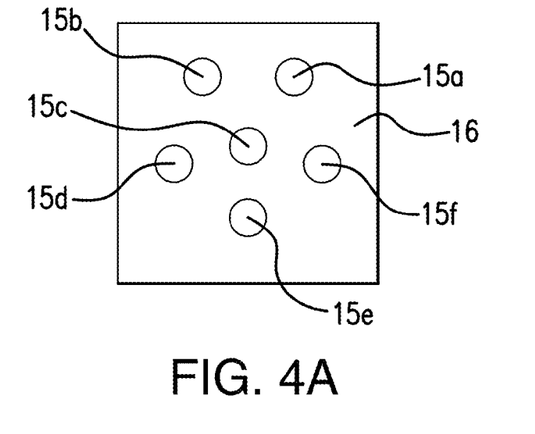
FIG. 4A is a schematic illustration of a sensor substrate with sensors disposed thereon to be used in conjunction with the optical detection system shown in FIG. 4.

In certain alternative embodiments, the sensor array is designed such that each sensor is made up of quantum dots having emission wavelengths different from the other sensors' emission wavelengths. In such instances, all of the sensors/sensing films are excited by a common excitation light source 122 as shown in FIG. 4. FIG. 4 provides an example of the set up for a system where the quantum dots associated with each of the six sensors are unique from the quantum dots associated with the other sensors. In that case, the six sensors 15a-15f are disposed on a common substrate 16 as shown in FIG. 4A. As shown in FIG. 4, when the quantum dots of the various sensors each have a different emission wavelength, a single probe 18 fed by an optical fiber is used to impinge excitation light onto the sensors 15a-15f disposed on substrate 16. The probe 18 also has a plurality of optical fibers for receiving and transmitting emission light to a detector 26 (a spectrometer) which reads the emission intensities of different QD fluorescence at different wavelengths. In such cases, there must be enough of a difference between the individual wavelengths of the QDs to avoid interference. The spectrometer scans a wavelength range of, for example, 480 nm-700 nm.

As shown in FIG. 4, emission and excitation light rays 50 are exchanged between the probe 18 and sensing films. An excitation source 122 transmits excitation light, via the optical fiber for excitation light 18a (shown in FIG. 5), such that excitation light passes through substrate 16 to excite the respective sensors 15 (a-f). The emission light is collected by and transmitted through optical fibers for emission light 18b (shown in FIG. 5) and a signal detector 26 measures the fluorescence signal which is subsequently processed by the data processor 40 to determine the rate of change. The sensing film with a single substrate 16 and six sensors 15a-15f shown in FIGS. 4 and 4A is provided for exemplary purposes only. The number of sensors utilized may vary depending upon the particular application and objectives.

When the sensor is placed in the presence of a chemical vapor, reaction between the polymer and the chemical will cause the polymer network to expand or contract. When impinged by an excitation light, an expanded polymer network will result in a correspondingly stronger fluorescent emission. On the other hand, contraction of the polymer network will generate a weaker fluorescent emission. Such expansion/contraction and the corresponding fluorescent emission intensity is shown in FIG. 1.

The sensor array can be applied to a wide variety of sensing applications. For instance, in an embodiment the sensor arrays can be used for chemical vapor detection, classification, and identification. The array is capable of discriminating different chemical vapors and can thus classify and identify chemical vapors that may be noxious. The array is therefore helpful in applications designed to detect toxic chemical contamination in air or those designed to warn of a chemical leak from a sealed container.

Additionally, in another embodiment the sensor array can be utilized for the detection of biological agents via sensing their volatile metabolites. Viable biological agents produce certain metabolites. *E. coli* cells, for example, produce indole which is a volatile organic compound. The sensor array can be designed to detect indole and therefore serve as a useful tool for screening for the presence of *E. coli* bacteria.

Furthermore, other embodiments encompass the sensor array applied to disease diagnosis via detection of particular human odor markers. Patients with certain diseases are known to have higher concentrations of certain volatile organic compounds present in their bodily fluids. Therefore, by testing a patient's breath, sweat, or urine, for example, the sensor array can be utilized for disease detection. By way of example, higher concentrations of acetone and methylethylketone, n-propanol, to name a few, are detectable in the breath of patients with lung carcinoma. The sensor array can be utilized to detect the target compounds for screening such medical conditions and therefore serve as a useful tool for early detection and treatment.

Example 1

In one working embodiment, a QD-polymer nanocomposite sensor array is made up of six sensors. Each of the sensors includes a plurality of quantum dots and a different polymer corresponding to each of the six sensors. Sensor 1 includes quantum dots doped in a PMMA polymer while sensor 2 includes quantum dots doped in a PVP polymer. Sensor 3 includes quantum dots doped in a PEG polymer and Sensor 4 includes quantum dots doped in a Polycaprolactone polymer. Sensor 5 includes quantum dots doped in a HPC polymer and Sensor 6 includes quantum dots doped in a Polystyrene co allyl alcohol polymer.

Each sensor of the array is formed by a different nanocomposite film. Each film was created by first obtaining a mass of each of the six different polymers (PMMA, PVP, PEG, Polycaprolactone polymer, HPC and Polystyrene co allyl alcohol) and a QD suspension. To form the QD suspension, QDs having a CdSe/ZnS core-shell ratio were purchased from Sigma Aldrich (product #694622) and the QDs were stabilized with Hexadecylamine (HAD) ligand surface coating to have a fluorescence emission wavelength of 590 nm. Each of the six polymers were mixed with a specific solvent as set forth in TABLE 2.1.

TABLE 2.1

| Sensor | Polymer | Solvent |
|---|---|---|
| 1 | PMMA | Toluene |
| 2 | PVP | Water |
| 3 | PEG | Water |
| 4 | Polycaprolactone | Tetrahydrofuran |
| 5 | HPC | Water |
| 6 | Polystyrene co allyl alcohol | Tetrahydrofuran |

While TABLE 2.1 provides for using one particular solvent corresponding to each of the 6 polymers, it will be apparent to those skilled in the art that alternative solvents having the same or similar chemical properties may be utilized so long as the polymer is capable of dissolving in the solvent chosen. For instance, rather than using water with the PVP and PEG of Sensors 2 and 3, ethanol could be used. Similarly, for sensor 4, rather than using tetrahydrofuran one may substitute chloroform or ethylacetate. For sensor 5, water was mixed with HPC but alcohol and anhydrous systems, for instance, polar organic solvents and glycols are acceptable alternatives.

In some instances, the polymer may swell when it comes into contact with the solvent. If swelling occurs, the mixture is given a period of time to sit and allow the swelling to subside. For example, the mixture may be allowed to sit overnight or for an equivalent period of time, such as approximately eight hours. In designing the sensors of the six sensor array, mixing was accomplished by vortexing for five minutes until a clear polymer solution was obtained. Alternative methods of mixing such as shaking and sonicating can also be employed. The length of time for mixing may vary dependent upon the combination of polymer and solvent used but, regardless of the method of mixing used, mixing should be carried out until the color of the mixture is homogenous.

Each of the 6 polymers and solvents were mixed in the ratio of 1.0 g polymer to 40 ml solvent until a clear polymer solution resulted. Then, the QD suspension having a concentration of 5 mg/ml was dried until the solution adopted a wax-like appearance. Thereafter, the dried QDs were added to each of the polymer solutions and were mixed to form precursor solutions. A portion of each precursor solution was deposited onto a substrate (in this case a glass slide was used) and spread thereupon. Finally, the precursor solutions were air-dried to form quantum dot-polymer nanocomposite sensing films. The amount of time required to dry the suspension is dependent upon the type of polymer and solvents used. For instance, PEG in ethanol may dry after a few minutes while PEG in water takes approximately one hour.

The 6 sensor array was utilized to determine combined responses to 9 different chemical vapors, namely, acetic acid, acetone, ethyl acetate, chlorobenzene, methanol, ethanol, isopropanol, toluene and xylene. Since each of the sensor films were created using QDs with 590 nm fluorescence emission wavelength, the detection system utilized 6 probes—each probe designed to individually excite the sensor films allowing for independent detection of changes in fluorescence emission intensity of each sensor. A schematic of the optical detection system employed is shown in FIG. 3. As seen in FIG. 3 each of the six sensor films is associated with a unique probe 18 and detection system 126 and the information obtained is detected by a common data processor 40 as previously discussed herein.

To test the sensor array response to chemical vapors, the array was first exposed to ambient air for 10 minutes. The length of time during which the array is exposed to ambient conditions may be adjusted based upon alternative experimental conditions such as, for example, use of different polymers. During exposure to ambient air, the fluorescence intensity of each sensor of the array was measured every 30 seconds. Thereafter, the array was exposed to one of the 9 different chemicals, namely, acetic acid, acetone, ethyl acetate, chlorobenzene, methanol, ethanol, isopropanol, toluene and xylene, and fluorescence was measured every 30 seconds. While measurements were taken in 30 second increments, it will be appreciated that alternative sampling rates may be employed. The optimal data sampling rate is dependent upon the particular application and may be adjusted accordingly.

Figure 6A:
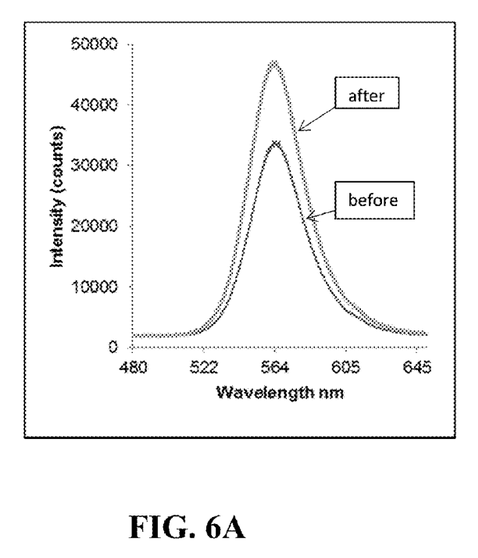
FIG. 6A is a graphical representation of the fluorescence spectra of a QD/PEG sensor film before and after exposure to acetone.
Figure 6B:
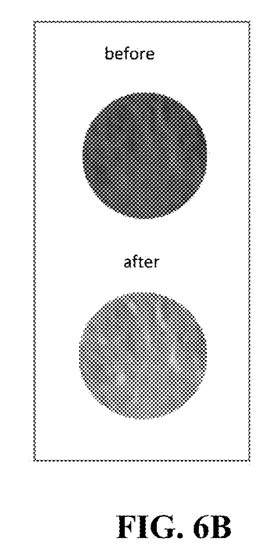
FIG. 6B is a fluorescence microscope image showing a QD/PEG sensor film before and after exposure to acetone.

FIG. 6A provides a graphical representation of the fluorescence spectra of a QD/PEG sensor (sensor 3) before and after exposure to acetone. The lower peak and higher peak represent fluorescent intensity before and after exposure to acetone, respectively. Such fluorescence is also evidenced in FIG. 6B which is a fluorescence microscope image showing a QD/PEG sensor film before and after exposure to acetone. The increase in fluorescent intensity of the QD/PEG sensor indicates that the polymer network expands in the presence of acetone.

The data shown in FIG. 6A is representative of the data obtained from each measurement (raw data). This data is used for data processing wherein the first step is to integrate the peak to obtain emission intensity for each data point (each measurement). The change rate is then calculated using three consecutive data points.

Three data points prior to chemical exposure were used to calculate the pre-exposure signal change rate (r1) and three data points after chemical exposure were used to calculate the post-exposure signal change rate (r2). This process was repeated until data was obtained for each of the 9 chemical vapors set forth in TABLE 2.1. The difference in the signal change rate prior to and after chemical vapor exposure (r2−r1) was calculated for each sensor and then normalized using the highest difference as 100 or −100. The normalized response for each independent sensor of the array to the 9 chemical vapors tested is reflected in TABLE 2.2 and graphically depicted in FIG. 7.

TABLE 2.2

| Polymer Used in Each Sensor | Acetic Acid | Acetone | Ethyl Acetate | Chlorobenzene | Methanol | Ethanol | Isopropanol | Toluene | Xylene |
| --- | --- | --- | --- | --- | --- | --- | --- | --- | --- |
| Sensor 1: PMMA | −43.95 | 1.01 | −2.08 | −1.08 | −23.10 | −13.10 | −3.10 | 3.94 | 4.68 |
| Sensor 2: PVP | −97.50 | 11.91 | 5.09 | −100.00 | 65.00 | 12.00 | 4.00 | 20.54 | 12.58 |
| Sensor 3: PEG | −20.44 | 100.00 | 7.79 | 2.79 | 25.61 | −22.61 | −12.61 | 12.20 | 3.58 |
| Sensor 4: Polycaprolactone | −50.40 | 52.06 | −7.99 | −3.99 | 98.15 | 93.15 | 3.15 | 100.00 | 35.55 |
| Sensor 5: HPC | −100.00 | 42.29 | −2.09 | −5.09 | −100.00 | −100.00 | −1.06 | 18.49 | −100.79 |
| Sensor 6: Polystyrene coallyl alcohol | 7.68 | −6.66 | 100.00 | −1.90 | −23.57 | 3.57 | 100.00 | −10.58 | −0.29 |

As can be seen in TABLE 2.2, sensor 4 elicited a normalized response which was a high, "positive response" (98.15) to methanol. This positive response, which can be seen with reference to FIG. 7, shows that there was an increase in fluorescence when sensor 4 was placed in the presence of the chemical of interest, namely, methanol Such a positive response indicates that the polycaprolactone polymer network of sensor 4 expanded in the presence of methanol. In contrast, sensor 5 elicited a normalized response which was a low, "negative response" (−100.00) to methanol. This negative response, which can also be seen with reference to FIG. 7, shows that there was a decrease in fluorescence when sensor 5 was placed in the presence of methanol Such a negative response indicates that the HPC polymer network of sensor 5 contracted in the presence of methanol. Finally, a positive or negative response may be obtained which is close to zero, for instance, the response of sensor 1 to acetone (1.01) and ethyl acetate (−2.08). Such minor changes in fluorescence are at noise level and are considered negligible. Therefore, the measured responses of sensor 1 to acetone and ethyl acetate indicate that the PMMA polymer network of sensor 1 neither expanded nor contracted in the presence of acetone or ethyl acetate.

Then, using the normalized response from each sensor as an element, the combined response from all 6 sensors can be expressed by a vector. For instance, the combined response for acetic acid is [−43.95, −97.50, −20.44, −50.40, −100.00, 7.68].

Example 2

In another working embodiment, a QD-polymer nanocomposite sensor array includes ten sensors. Each of the sensors includes a plurality of quantum dots and a different polymer. Sensors 1-5 include quantum dots doped into the same polymers as specified for Sensors 1-5 in the 6 sensor array above. In addition, sensor 6 includes quantum dots doped in a poly (allylamine hydrochloride) polymer and sensor 7 includes quantum dots doped in a poly(carbonate bisphenol A) polymer. Sensors 8, 9 and 10 include quantum dots respectively doped in a poly(ethylene-co-vinly acetate) polymer, a polysulfone polymer, and a poly(sodium 4-styrenesulfonate) polymer.

Each sensor of the array is formed by a different nanocomposite film and each film was created by the methodology outlined with respect to EXAMPLE 1. The first five sensors of the ten sensor array are the same as those in the six sensor array previously described herein. The ten polymers were respectively mixed with the solvents as set forth in TABLE 3.1.

TABLE 3.1

| Sensor | Polymer | Solvent |
|---|---|---|
| 1 | PMMA | Toluene |
| 2 | PVP | Water |
| 3 | PEG | Water |
| 4 | Polycaprolactone | Tetrahydrofuran |
| 5 | HPC | Water |
| 6 | Poly(allylamine hydrochloride) | Water |
| 7 | Poly(carbonate bisphenol A) | Carbon tetrachloride |
| 8 | Poly(ethylene-c-vinyl acetate) | Tetrahydrofuran |
| 9 | Polysulfone | Carbon tetrachloride |
| 10 | Poly(sodium 4-styrenesulfonate) | Water |

While TABLE 3.1 provides for using one particular solvent corresponding to each of the 10 polymers, it will be apparent to those skilled in the art that alternative solvents may be utilized. For example, the same substitutions for sensors 2, 3 and 4 can be made as previously discussed herein with regard to EXAMPLE 1. For sensor 7, Poly (carbonate bisphenol A) may be mixed with a variety of different chlorinated solvents such as methylene chloride in place of carbon tetrachloride. Similarly, the polysulfone polymer of sensor 9 may be mixed with tetrahydrofuran, dimethyl sulfoxide or another hexane chlorinated hydrocarbon such as dichloromethane in place of the carbon tetrachloride which was used in the 10 sensor array.

The 10 sensor array was tested to determine combined responses to 8 different chemical vapors, namely, 2-methylpentane, acetic acid, acetone, ethanol, indole, pentane, toluene and water. As in EXAMPLE 1, combined responses were obtained by first exposing the array to ambient air for 10 minutes. During exposure to ambient air, the fluorescence intensity of each sensor of the array was measured every 30 seconds. Thereafter, the array was exposed to one of the 8 different chemicals, namely, 2-methylpentane, acetic acid, acetone, ethanol, indole, pentane, toluene and water, and fluorescence was measured every 30 seconds. Three data points prior to chemical exposure were used to calculate the pre-exposure signal change rate (r1) and three data points after chemical exposure were used to calculate the post-exposure signal change rate (r2). This process was repeated until data was obtained for each of the 8 chemical vapors set forth in TABLE 3.1.

The difference in the signal change rate prior to and after chemical vapor exposure (r2−r1) was calculated for each sensor and then normalized using the highest difference as 100 or −100. The normalized response for each independent sensor of the array to the 8 chemical vapors tested is reflected in TABLE 3.2 and graphically depicted in FIG. 8.

TABLE 3.2

| Polymer Used in Each Sensor | 2-Methylpentane | Acetic Acid | Acetone | Ethanol | Indole | Pentane | Toluene | Water |
|---|---|---|---|---|---|---|---|---|
| Sensor 1: PMMA | 0.13 | −25.33 | 2.01 | −7.38 | −23.21 | −100.00 | 3.94 | 1.40 |
| Sensor 2: PVP | 8.65 | −52.76 | 14.14 | 6.76 | −39.33 | 32.21 | 20.54 | 11.13 |
| Sensor 3: PEG | −6.69 | −9.85 | 100.0 | −12.73 | 42.79 | −4.32 | 12.20 | −100.00 |
| Sensor 4: Polycaprolactone | 9.47 | −26.76 | 55.06 | 52.44 | 44.77 | 24.07 | 100.00 | 6.37 |
| Sensor 5: HPC | 4.23 | −53.09 | 43.29 | −56.30 | 9.61 | −29.82 | 18.49 | 3.42 |
| Sensor 6: poly(allylamine hydrochloride) | 12.61 | −4.81 | 49.79 | −23.06 | 42.53 | 34.17 | −0.35 | 15.73 |
| Sensor 7: poly(carbonate bisphenol A) | −12.65 | −100.00 | 69.89 | 100.00 | 44.77 | 49.25 | 16.78 | −4.75 |
| Sensor 8: poly(ethylene-co-vinyl acetate) | −30.49 | 29.69 | 45.80 | −0.17 | 100.00 | 4.89 | 23.66 | 18.45 |

TABLE 3.2-continued

| Polymer Used in Each Sensor | 2-Methyl-pentane | Acetic Acid | Acetone | Ethanol | Indole | Pentane | Toluene | Water |
|---|---|---|---|---|---|---|---|---|
| Sensor 9: polysulfone | 100.00 | −49.67 | 8.34 | −21.30 | −12.33 | 84.68 | 34.24 | 13-21 |
| Sensor 10: poly(sodium 4-styrenesulfonate) | 4.84 | −5.73 | 6.42 | −13.17 | 18.31 | 7.43 | 0.47 | −11.14 |

As can be seen in TABLE 3.2, sensor 7 elicited a normalized response which was a high, "positive response" (100.00) to ethanol. This positive response, which can be seen with reference to FIG. 8, shows that there was an increase in fluorescence when sensor 7 was placed in the presence of the chemical of interest, namely, ethanol Such a positive response indicates that the poly(carbonate bisphenol A) polymer network of sensor 7 expanded in the presence of ethanol. In contrast, sensor 7 elicited a normalized response which was a low, "negative response" (−100.00) to acetic acid. This negative response, which can also be seen with reference to FIG. 8, shows that there was a decrease in fluorescence when sensor 7 was placed in the presence of acetic acid. Such a negative response indicates that the poly(carbonate bisphenol A) polymer network of sensor 7 contracted in the presence of acetic acid. Finally, a positive or negative response may be obtained which is close to zero, for instance, the response of sensor 10 (0.47) and the response of sensor 6 (−0.35) to toluene. Such minor changes in fluorescence are at noise level and are considered negligible. Therefore, the measured responses of sensors 6 and 10 to toluene indicate that the poly(allylamine hydrochloride) polymer of sensor 6 and the poly(sodium 4-styrenesulfonate) polymer of sensor 10 neither expanded nor contracted in the presence of toluene.

Then, using the normalized response from each sensor as an element, the combined response from all 10 sensors can be expressed by a vector. For instance, the combined response for 2-Methylpentane is [0.13, 8.65, −6.69, 9.47, 4.23, 12.61, −12.65, −30.49, 100.00, 4.48].

The descriptions above are intended to illustrate possible implementations of the present invention and are not restrictive. While this disclosure has been made in connection with specific forms and embodiments thereof, it will be appreciated that various modifications other than those discussed above may be resorted to without departing from the spirit or scope of the claimed invention. Such variations, modifications, and alternatives will become apparent to the skilled artisan upon review of the disclosure. For example, functionally equivalent elements or method steps may be substituted for those specifically shown and described, and certain features may be used independently of other features, and in certain cases, particular locations of elements or sequence of method steps may be reversed or interposed, all without departing from the spirit or scope of the invention as defined in the appended Claims. The scope of the claimed invention should therefore be determined with reference to the description above and the appended claims, along with their full range of equivalents.

What is claimed is:

1. A method of detecting the presence of a chemical vapor of interest from a group of chemical analytes of interest comprising:
   (a) manufacturing a plurality of quantum dot polymer nanocomposite sensing films, each of the sensing films comprising a plurality of quantum dots (QDs) having a CdSe/ZnS core-shell ratio doped into one of a plurality of different polymer networks to form a film, each of the plurality of different polymer networks having a characteristic of expanding or contracting in a predetermined manner responsive to exposure to at least one of the group of chemical analytes of interest, the plurality of different polymer networks being selected to provide, in combination, a contraction/expansion response to each chemical analyte of the group of chemical analytes of interest that identifies, which chemical analyte is being sensed;
   (b) impinging the plurality of quantum dot polymer nanocomposite films by an excitation light source;
   (c) exposing the plurality of sensing films to a suspected contaminant;
   (d) detecting a change in fluorescence emission intensity from the films resulting from the contraction or expansion of the polymer network responsive to the excitation light source over time and the exposure to the suspected contaminant; and
   (e) comparing the change in fluorescence emission intensity from the plurality of sensing films to establish a unique combined response.

2. The method of detecting the presence of a chemical vapor of interest as claimed in claim 1, wherein the QDs of each of the plurality of sensing films have different emission wavelengths and the sensing films are excited by a common excitation light source.

3. The method of detecting the presence of a chemical vapor of interest as claimed in claim 1, wherein each of the sensors are comprised of QDs having the same emission wavelengths and the sensing films are individually excited and the changes in fluorescence emission intensity of each sensor is separately detected.

4. A method of detecting at least one target chemical vapor analytes of interest from a group of target chemical analytes, comprising:
   providing an array of quantum-dot polymer nanocomposite sensors on a substrate, each of said sensors of said array including a different selected polymer network of a group of a plurality polymer networks and a quantum dot suspension, the group of polymer networks being selected to detect one or more of the group of target chemical analytes in a gas sample, the quantum dot suspension comprising QDs having a CdSe/ZnS core-shell ratio;
   exposing said array of quantum-dot polymer nanocomposite sensors to the gas sample, wherein exposure to said gas sample causes a corresponding expansion or contraction of the polymer network;
   providing an optical detection system including at least one source of excitation light and impinging said excitation light upon said array of quantum-dot polymer nanocomposite sensors during said exposure to the gas sample, and at least one optical detector receiving emitted fluorescence from said array of quantum-dot polymer nanocomposite sensors; and analyzing the emitted fluorescence of said array of quantum-dot polymer nanocomposite sensors collectively to identify one or more of the group of target chemical vapor analytes of interest in the gas sample.

5. The method of detecting chemical vapors in a gas sample as cited in claim 4, where said step of impinging said excitation light upon said array of quantum-dot polymer nanocomposite sensors includes the step of using a single excitation light source to impinge said excitation light upon said array of quantum-dot polymer nanocomposite sensors.

6. The method of detecting chemical vapors in a gas sample as cited in claim 5, where said step of receiving emitted fluorescence from said array of quantum-dot polymer nanocomposite sensors includes the step of using a single optical detector to receive emitted fluorescence from said array of quantum-dot polymer nanocomposite sensors.

7. The method of detecting chemical vapors in a gas sample as cited in claim 4, where said step of impinging said excitation light upon said array of quantum-dot polymer nanocomposite sensors includes the step of using a plurality of excitation light sources, each excitation light source separately impinging excitation light therefrom upon a corresponding one of said sensors of said array of quantum-dot polymer nanocomposite sensors.

8. The method of detecting chemical vapors in a gas sample as cited in claim 7, where said step of receiving emitted fluorescence from said array of quantum-dot polymer nanocomposite sensors includes the step of using a plurality of optical detectors, each optical detector separately receiving emitted fluorescence from a corresponding one of said sensors of said array of quantum-dot polymer nanocomposite sensors.

* * * * *